US012115704B2

(12) United States Patent
DeSoutter et al.

(10) Patent No.: US 12,115,704 B2
(45) Date of Patent: Oct. 15, 2024

(54) IMPRESSION ELEMENT FOR THE CREATION OF A SURGICAL GUIDE

(71) Applicant: Prometheus Surgical Limited, Buckinghamshire (GB)

(72) Inventors: George DeSoutter, Buckinghamshire (GB); William DeSoutter, Buckinghamshire (GB); Ryan Fenton, Buckinghamshire (GB); Christopher Block, Buckinghamshire (GB)

(73) Assignee: Prometheus Surgical Limited, Buckinghamshire (GB)

( * ) Notice: Subject to any disclaimer, the term of this patent is extended or adjusted under 35 U.S.C. 154(b) by 265 days.

(21) Appl. No.: 17/436,168

(22) PCT Filed: Mar. 12, 2020

(86) PCT No.: PCT/GB2020/050632
§ 371 (c)(1),
(2) Date: Sep. 3, 2021

(87) PCT Pub. No.: WO2020/183186
PCT Pub. Date: Sep. 17, 2020

(65) Prior Publication Data
US 2022/0134624 A1 May 5, 2022

(30) Foreign Application Priority Data
Mar. 12, 2019 (GB) ..................... 1903389

(51) Int. Cl.
*B29C 43/18* (2006.01)
*B29C 31/04* (2006.01)
(Continued)

(52) U.S. Cl.
CPC ............ *B29C 43/18* (2013.01); *B29C 31/041* (2013.01); *B29C 33/0038* (2013.01);
(Continued)

(58) Field of Classification Search
CPC .............. B29C 31/041; B29C 33/0038; B29C 33/0061; B29C 33/0077; B29C 33/10;
(Continued)

(56) References Cited

U.S. PATENT DOCUMENTS 5,037,445 A 8/1991 Sander et al.
9,125,673 B2 9/2015 Fitz et al.
(Continued)

FOREIGN PATENT DOCUMENTS

EP 0398497 A1 11/1990
JP H06238710 A 8/1994
(Continued)

OTHER PUBLICATIONS

International Preliminary Report on Patentability dated Sep. 23, 2021 in connection with International Patent Application No. PCT/GB2020/050632, 7 pages.
(Continued)

*Primary Examiner* — Robert B Davis
(74) *Attorney, Agent, or Firm* — Dorsey & Whitney LLP

(57) ABSTRACT

According to an aspect of the invention there is provided a mouldable material carrier for use in producing an impression of a surgical site comprising: a base having a channel passing through the base between an inlet and an outlet; and a securing portion configured to secure a flexible sheet to the base around the outlet to cover the outlet such that, when mouldable material is urged through the inlet, the mouldable material is extruded out of the outlet and contained within a volume defined by the flexible sheet and the base, such that when the mouldable material carrier is urged against a surgical site, the mouldable material within the volume forms an impression of the surgical site without making contact with the surgical site.

19 Claims, 11 Drawing Sheets

(51) Int. Cl.
    *B29C 33/00*     (2006.01)
    *B29C 33/10*     (2006.01)
    *A61B 17/00*     (2006.01)
    *A61B 17/15*     (2006.01)
    *A61B 17/17*     (2006.01)
    *A61B 17/56*     (2006.01)
    *B29C 48/25*     (2019.01)
    *B29C 48/345*     (2019.01)
    *B29L 31/00*     (2006.01)

(52) U.S. Cl.
    CPC .......... *B29C 33/0061* (2013.01); *B29C 33/10* (2013.01); *A61B 2017/00526* (2013.01); *A61B 17/15* (2013.01); *A61B 17/17* (2013.01); *A61B 2017/568* (2013.01); *B29C 2043/189* (2013.01); *B29C 48/25* (2019.02); *B29C 48/254* (2019.02); *B29C 48/345* (2019.02); *B29L 2031/7546* (2013.01)

(58) Field of Classification Search
    CPC .............. B29C 43/18; B29C 2043/189; A61B 2017/568
    USPC .............................................. 425/2, 89, 449
    See application file for complete search history.

(56) References Cited

U.S. PATENT DOCUMENTS

| | | | |
|---|---|---|---|
| 2012/0116523 A1* | 5/2012 | Forsell | A61F 2/30721 |
| | | | 425/2 |
| 2013/0236874 A1 | 9/2013 | Iannotti et al. | |
| 2015/0118338 A1 | 4/2015 | Galfione | |
| 2016/0342766 A1 | 11/2016 | Darwood | |

FOREIGN PATENT DOCUMENTS

| | | |
|---|---|---|
| JP | 2005035462 A | 2/2005 |
| JP | 2015509810 A | 4/2015 |
| WO | 2015075423 A2 | 5/2015 |

OTHER PUBLICATIONS

International Search Report and Written Opinion dated Jun. 9, 2020 in connection with International Patent Application No. PCT/GB2020/050632, 11 pages.

Examination Report dated Aug. 12, 2019 in connection with British patent application No. 1903389.3, 5 pages.

Office Action dated Oct. 16, 2023 in connection with Japanese patent application No. 2021-553305, 18 pages including English translation.

* cited by examiner

IMPRESSION ELEMENT FOR THE CREATION OF A SURGICAL GUIDE

This application is a U.S. National Stage Application of International Patent Application No. PCT/GB2020/050632, filed Mar. 12, 2020, which claims priority to British Patent Application No. 1903389.3, filed Mar. 12, 2019, each of which is incorporated by reference herein, in the entirety and for all purposes.

TECHNICAL FIELD

The present disclosure relates to mouldable material carriers for use in producing impressions of surgical sites. In particular, but without limitation, this disclosure relates to mouldable material carriers for use in forming surgical guides from impressions of surgical sites.

BACKGROUND

In order for a successful surgical plan to be executed, particularly in orthopaedics, it is accurate placement of surgical implants and prostheses are critical. Surgical guides are used in surgery to help guide the surgeon to cut or drill along the correct direction and/or plane. For instance, in hip and knee replacements, surgical guides are often provided with guide holes to help guide the surgeon to drill holes into the surgical site in the correct position and along the correct axis. This ensures that the implant is fitted accurately and reliably.

In the medical field, dentistry and orthopaedics in particular, patient specific instrumentation such as bespoke surgical guides have been made using rapid manufacturing and prototyping techniques (such as via additive manufacturing). These bespoke surgical guides are required to precisely fit a specific part of a unique patient's anatomy (the surgical site), as any inaccuracies in the fit can result in inaccuracies in the surgical procedure.

For the bespoke surgical guide to accurately fit the patient's anatomy and provide an accurate guide for the implant to be inserted, the manufacturing and prototyping systems need to be provided with reliable surface data of the surgical site with minimal errors. Where the surgical site needs to be operatively exposed during surgery (i.e. where incisions are required to access the surgical site) this data can be provided via pre-operative scans of the patient, such as computed tomography (CT) scans or magnetic resonance imaging (MRI) scans. Having said this, traditional rapid manufacturing and prototyping techniques, such as additive manufacturing, suffer from multiple disadvantages that hinder the accuracy and logistics of surgical guide fabrication.

Many rapid manufacturing and prototyping techniques require bespoke equipment and take time to fabricate such that the surgical guide needs to be fabricated offsite in advance of the surgery. This limits the options for the surgeon during surgery, confining the surgeon to the predefined surgical plan. Most importantly, such prefabricated guides often do not accurately fit the surgical site during surgery. This is because, where the surgical site is within the body of the patient, it is only exposed during surgery. The surgical guide is therefore formed from a scan of the patient and, in this case, the surface data may not reflect the actual surface of the surgical site during the procedure. This is because the guide may be fabricated on the assumption that all soft-tissue is removed from the site (e.g. based on scans showing the surface of a bone, such as a hip bone, within the surgical site); however, in practice, the surgeon may not remove all soft tissue. For instance, CT scans may fail to show cartilage which may be present in the impression surface. Furthermore, whilst MRI scans show cartilage, the segmentation process (the process of extracting the relevant portions of the scan relating to the surgical site) is more difficult for MRI scans due as a boundary threshold must be used, rather than a volumetric threshold as in CT scans. In this case, the remaining soft tissue can cause the prefabricated surgical guide to fit poorly within the surgical site, causing inaccuracies in the surgical procedure. In some cases, surgeons have been known to discard surgical guides completely during surgery and operate without a guide due to the poor quality of the fit.

It is also possible to form a surgical guide from an impression of a surgical site. Mouldable material such as silicone impression material or thermoplastic material may be used to take an impression. The impression may be modified after the material has set in order to produce a surgical guide (e.g. through drilling guide holes within the impression). This is effective as the portion of the surgical guide that couples to the surgical site is a direct impression of the surgical site. This removes the errors and uncertainty associated with rapid manufacturing and prototyping, and allows the surgical guide to be formed during surgery, providing additional speed and flexibility; however, there are issues associated with obtaining an accurate mould of a surgical site. The mould requires a tight fitting around the surgical site to obtain an impression with enough detail to extract surface data. Moreover, some of the mouldable material may be undesirably deposited onto the surgical site. This could lead to contamination of the surgical site. Accordingly, there is a need for an improved means of obtaining an impression of a surgical site for use in producing a surgical guide.

SUMMARY

The present invention seeks to provide an improved impression element for the creation of a surgical guide.

According to an aspect of the invention there is provided a mouldable material carrier for use in producing an impression of a surgical site comprising: a base having a channel passing through the base between an inlet and an outlet; and a securing portion configured to secure a flexible sheet to the base around the outlet to cover the outlet such that, when mouldable material is urged through the inlet, the mouldable material is extruded out of the outlet and contained within a volume defined by the flexible sheet and the base, such that when the mouldable material carrier is urged against a surgical site, the mouldable material within the volume forms an impression of the surgical site without making contact with the surgical site.

As the mouldable material within the volume forms an impression of the surgical site without making contact with the surgical site, the surgical site will not be contaminated by the mouldable material. Having the flexible sheet around the outlet will also ensure that mouldable material will not be deposited onto the surgical site after an impression has been taken. Furthermore, as the flexible sheet contains the mouldable material within the mouldable material carrier, the mouldable material cannot escape the vicinity of the surgical site as the impression is taken. Accordingly, the mouldable material is compressed as the impression is taken; thereby, providing a more accurate impression. Furthermore, containing the mouldable material within a flexible sheet makes the mouldable material carrier easier to use, as the user need not worry about the mouldable material falling out of the carrier.

The securing portion may releasably or non-releasably secure the flexible sheet. That is, the sheet may form an integral part of the mouldable material carrier, or may be removable. Where the securing portion releasably secures the flexible sheet to the base, the flexible sheet may be detached from the base. This allows the flexible sheet to be removed after an impression has been taken in order to allow the surface of the impression to be more accurately scanned and modified, and to ensure a more accurate and secure fit between the impression and the surgical site.

The securing portion may be a clip, clamp, screw or any other suitable securing system that will enable the flexible sheet to be secured to the base.

The flexible sheet may comprise a pull tab to aid the removal of the flexible sheet from the base. The flexible sheet may be a membrane. Having a pull tab can assist with the removal of the flexible sheet from the base. This may be particularly advantageous in a surgical environment as many medical practitioners are required to wear disposable gloves or other garment that may create difficulties in removing the flexible sheet.

The base may be substantially rigid, although, need not be completely rigid. The base may have some degree of flexibility whilst still achieving the main functions of the mouldable material carrier to house the mouldable material and provide a carrier for allowing an impression of a surgical site to be taken.

The mouldable material may be initially mouldable to allow an impression to be taken; however, the mouldable material may be configured to harden or set in order to maintain its form after the impression has been formed.

Advantageously, the securing portion may be configured to form a seal around the outlet between the flexible sheet and the base.

Forming a seal around the outlet, between the flexible sheet and the base, ensures that mouldable material cannot escape between the flexible sheet and base. This provides a tighter confinement of the mouldable material inside the volume.

The seal being formed around the outlet means that the seal is formed along a continuous path that encircles or surrounds the outlet. There need not be direct contact between the seal and the outlet. The seal may be sufficient to prevent mouldable material from passing between the flexible sheet and the base; however, the seal need not be fluid or air-tight. The seal may be formed through the securing portion clamping the flexible sheet against the base.

Advantageously, the mouldable material carrier may further comprise the flexible sheet secured to the base to cover the outlet. That is, the flexible sheet may form part of the mouldable material carrier.

Advantageously, the flexible sheet may be elastic. The flexible sheet may have a Young's modulus of between 0.1 and 0.01 GPa, although other levels of elasticity may be used. Having an elastic flexible sheet ensures that the flexible sheet provides a reactionary force against the insertion of the mouldable material as the mouldable material stretches the flexible sheet. This helps to compress the mouldable material within the volume so that a more accurate impression can be taken.

The flexible sheet may be biocompatible. As the flexible sheet will come into contact with a surgical site of a patient, it would be advantageous for the flexible sheet to be biocompatible to avoid harm to the patient.

Advantageously, the outlet may comprise at least one hole of reduced dimensions relative to the channel to resist the mouldable material from escaping the volume through the channel after the mouldable material has been urged into the volume.

Having the outlet comprise at least one hole of reduced dimensions relative to the channel increases the pressure requirement for the mouldable material to pass through the outlet in both directions. As the mouldable material can be forcefully urged into the volume by a user, the mouldable material will have enough force from the user to urge the mouldable material through the outlet and into the volume. However, when the mouldable material is inside the volume, the compressing force from the flexible sheet (or from the act of taking the impression) will not provide sufficient to overcome the pressure requirement imposed by the at least one hole of reduced dimensions relative to the channel. The outlet thus acts as a one-way valve, providing the advantageous effect of allowing mouldable material into the volume but resisting the escape of mouldable material.

Advantageously, the at least one hole may be a plurality of holes formed via a grating provided at the outlet. Providing a grating with a plurality of holes allows mouldable material to be urged into the volume at a faster rate whilst still resisting mouldable material from escaping the volume through the channel.

Advantageously, the plurality of holes may be evenly distributed across outlet. This provides an even distribution of mouldable material out of the outlet which, in turn, helps to provide an even distribution of mouldable material inside the volume. An even distribution of mouldable material helps to provide a more accurate impression of the surgical site.

Advantageously, the volume may be at least partly defined by the flexible sheet and a cavity formed within the base and around the outlet. That is, the flexible sheet may be secured over a cavity in the base. The cavity can provide a space in which the mouldable material can be, at least partially, housed. In addition, the cavity can help at least partially couple the mouldable material to the mouldable material carrier, particularly after the mouldable material has hardened. For instance, the cavity can resist the mouldable material moving within the mouldable material carrier at least transversely (e.g. via side-walls) if not also longitudinally (e.g. via transverse protrusions into the cavity). Whilst the mouldable material is still mouldable, the mouldable material may still be moveable around the cavity, but the walls of the cavity will resist the mouldable material from escaping the cavity, thereby at least partially coupling the mouldable material to the mouldable material carrier. When the mouldable material has set, the mouldable material will conform to the shape of the cavity and resistance by the set material from changing shape will at least partially couple the set material to the mouldable material carrier.

It is important that the mouldable material is effectively coupled to the mouldable material carrier, even if the mouldable material is also contained by the sheet. Firstly, it is important that relative movement of the mouldable material and carrier is limited to ensure that the impression can be effectively registered with a production apparatus and modified accurately to produce a surgical guide. Furthermore, secure coupling helps to aid in the accurate taking of the impression of the surgical site.

The cavity may be in fluid communication with the channel so that mouldable material enters the cavity when extruded through the outlet. The cavity may be at least partially defined by a wall surrounding the cavity. This may be in the form of a raised rim or flange around the periphery of the base. The cavity formed within the base and around the outlet may contain at least a portion of the mouldable material within the volume. Advantageously, the base may comprise at least one protrusion into the cavity to help couple the mouldable material to the mouldable material carrier and help resist the removal of the mouldable material from the cavity after the mouldable material has been urged into the cavity.

The at least one protrusion may protrude laterally into the cavity from the wall surrounding the cavity (e.g. a raised rim or flange around the periphery of the base). By "protruding laterally", it is meant that the protrusion protrudes along a direction that has at least a component that is in the lateral direction. Having the at least one protrusion protrude laterally into the cavity works synergistically with the sides (walls) of the cavity. Specifically, the sides of the cavity may be configured to resist transverse movements of the mouldable material and the at least one protrusion protruding laterally into the cavity may be configured to resist longitudinal movements of the mouldable material.

Advantageously, the channel may narrow along its length from the inlet to the outlet. The narrowing of the channel along its length from the inlet to the outlet prevents a mouldable material dispenser from being over-inserted. This protects the outlet, which may be prone to damage by over-insertion of a mouldable material dispenser. In addition, the narrowing of the channel can help provide a seal around the mouldable material dispenser to prevent the mouldable material passing back down the channel, past the tip of the mouldable material dispenser, and escaping out the inlet.

Additionally, the inlet may be bevelled to guide a user in the insertion of a mouldable material dispenser into the mouldable material carrier. This makes the system easier to use by helping the user align the mouldable material dispenser with the inlet. The bevelled portion of the inlet also reduces the risk of the mouldable material dispenser damaging the channel and inlet. This could happen through forceful insertion of the mouldable material dispenser. Structural defects within the interior of the mouldable material carrier could lead to inaccurate guiding channels.

Advantageously, at least one air hole may be formed through the base such that air within the volume may escape the volume through the at least one air hole as the mouldable material is urged into the volume. This helps ensure that air is not trapped within the volume which can affect the accuracy of the impression. The at least one air hole may be distributed evenly around the base. Even distribution of air holes prevents air from being accumulated in certain regions of the volume inside the mouldable material carrier. Over accumulation of air in certain regions of the volume will hinder the confinement of the mouldable material by the flexible sheet. This may lead to inaccurate impressions of surgical sites due to the added dimensions of excessive air inside the volume.

Advantageously, the securing portion may comprise an opening through which the flexible sheet is exposed when secured to allow an impression to be taken through the flexible sheet. For instance, the securing portion may be in the form of a retaining ring that secures over the periphery of the base whilst ensuring that the flexible sheet is exposed so that an impression can be taken. When mouldable material is inserted into the volume, the flexible sheet and mouldable material may protrude through the opening in the securing portion.

Advantageously, the securing portion may form part of one or both of the flexible sheet and the base.

For instance, the securing portion may form part of or be connected to the flexible sheet and may be configured to be releasably secured to the base. In this regard, the securing portion may be an elasticated section of the flexible sheet forming an opening into which the base may be secured. The opening may be smaller (e.g. have a smaller cross-section) than the base, so that the securing portion must be stretched over a periphery of the base in order to secure the flexible sheet to the base.

Alternatively, or in addition, the securing portion may form part of or be connected to the base. For instance, the securing portion may comprise a clamp, for clamping the flexible sheet to the base.

In addition to the above, the securing portion may be formed of two sections, a first section that forms part of the flexible sheet and a second section that forms part of the base. These two parts may interact in order to secure the flexible sheet to the base. For instance, one of the two sections may fit within the other (e.g. via an interference fit) in order to secure the flexible sheet to the base.

Advantageously, the securing portion may be separable from the base and may be configured to be secured over the base to releasably secure the flexible sheet to the base. This provides a clamping mechanism for clamping the flexible sheet to the base.

Advantageously, the securing portion may comprise a finger release tab for aiding a user to release the securing portion to separate the flexible sheet from the base. This can provide the user with purchase to aid in releasing the securing portion.

Advantageously, the securing portion may be configured to releasably secure the flexible sheet to the base. This allows the flexible sheet to be detached so that the surface of the impression can be scanned and modified by a production apparatus to produce a surgical guide, and so that the impression/surgical guide can be more securely fitted back into the surgical site.

Advantageously, the base may further comprise a coupling portion configured to couple the base to a production apparatus in a predetermined position and orientation so that, after an impression of a surgical site has been taken, a configuration of surface of the mouldable material can be recorded with respect to a known point of reference. This allows the surface of the impression to be scanned and the impression to be modified automatically by a production apparatus more accurately without the need to repeatedly recalibrate the system (without needing to repeatedly re-register the impression with the production apparatus). The coupling portion may be a coupling element that ensures that the base is secured to the production apparatus in a predefined position, orientation or configuration.

The mouldable material carrier may suitable for use in producing a surgical guide through modification of the mouldable material carrier through drilling or cutting. The base may be formed on material suitable for cutting or drilling to form guide-hole(s) for a surgical guide.

Advantageously, the mouldable material carrier may be modified to include a guiding channel for guiding a surgical component to interact with a surgical site. The mouldable material carrier may be used as the surgical guide itself. As the mouldable material carrier carries the impression of the surgical site, the mouldable material carrier can be repositioned onto the same surgical site to guide a surgical component through its guiding channel with a high degree of accuracy.

According to another aspect of the invention there is provided a kit of parts for producing a mouldable material carrier for use in obtaining an impression of a surgical site, including: a flexible sheet; a base having a channel passing through the base between an inlet and an outlet; and a securing portion configured to secure the flexible sheet to the base around the outlet to cover the outlet such that, when mouldable material is urged through the inlet, the mouldable material is extruded out of the outlet and contained within a volume defined by the flexible sheet and the base, such that when the mouldable material carrier is urged against a surgical site, the mouldable material within the volume forms an impression of the surgical site without making contact with the surgical site.

The kit of parts may further comprise mouldable material for being placed against a surgical site to form an impression of that site.

The securing portion of the kit of parts may form part of one or both of the flexible sheet and the base.

According to a further aspect there is provided a mouldable material carrier for use in obtaining an impression of a surgical site, including: a base and a securing portion configured to secure a flexible sheet to the base to contain mouldable material within a volume defined by the flexible sheet and the base, such that when the mouldable material carrier is urged against a surgical site, the mouldable material within the volume forms an impression of the surgical site without making contact with the surgical site. Advantageously, the securing portion may releasably secure the flexible sheet to the base.

According to a further aspect there is provided a kit of parts for producing a mouldable material carrier for use in obtaining an impression of a surgical site, including: a base and a flexible sheet comprising a securing portion configured to secure the flexible sheet to the base to contain mouldable material within a volume defined by the flexible sheet and the base, such that when the mouldable material carrier is urged against a surgical site, the mouldable material within the volume forms an impression of the surgical site without making contact with the surgical site. According to an embodiment, the securing portion of the flexible sheet is an opening of the flexible sheet, wherein the flexible sheet is elastic at least at the opening to allow the flexible sheet to be secured over the base. According to an embodiment, the flexible sheet comprises an inlet through which mouldable material may be urged into the volume.

BRIEF DESCRIPTION OF THE DRAWINGS

Embodiments of the present invention are described herein with reference to the accompanying figures, in which.

DETAILED DESCRIPTION

Embodiments described herein provide an improved mouldable material carrier for forming an impression of a surgical site for the creation of a surgical guide. More particularly, embodiments relate to an impression element that safely and effectively provides an accurate impression of a surgical site by allowing the retention of mouldable material within the mouldable material carrier through the use of a flexible sheet through which an impression may be taken. This helps to compact the mouldable material, particularly at the periphery, to provide a secure fit with the surgical site, as well as avoiding excess mouldable material from escaping into the surgical site.

Figure 1:
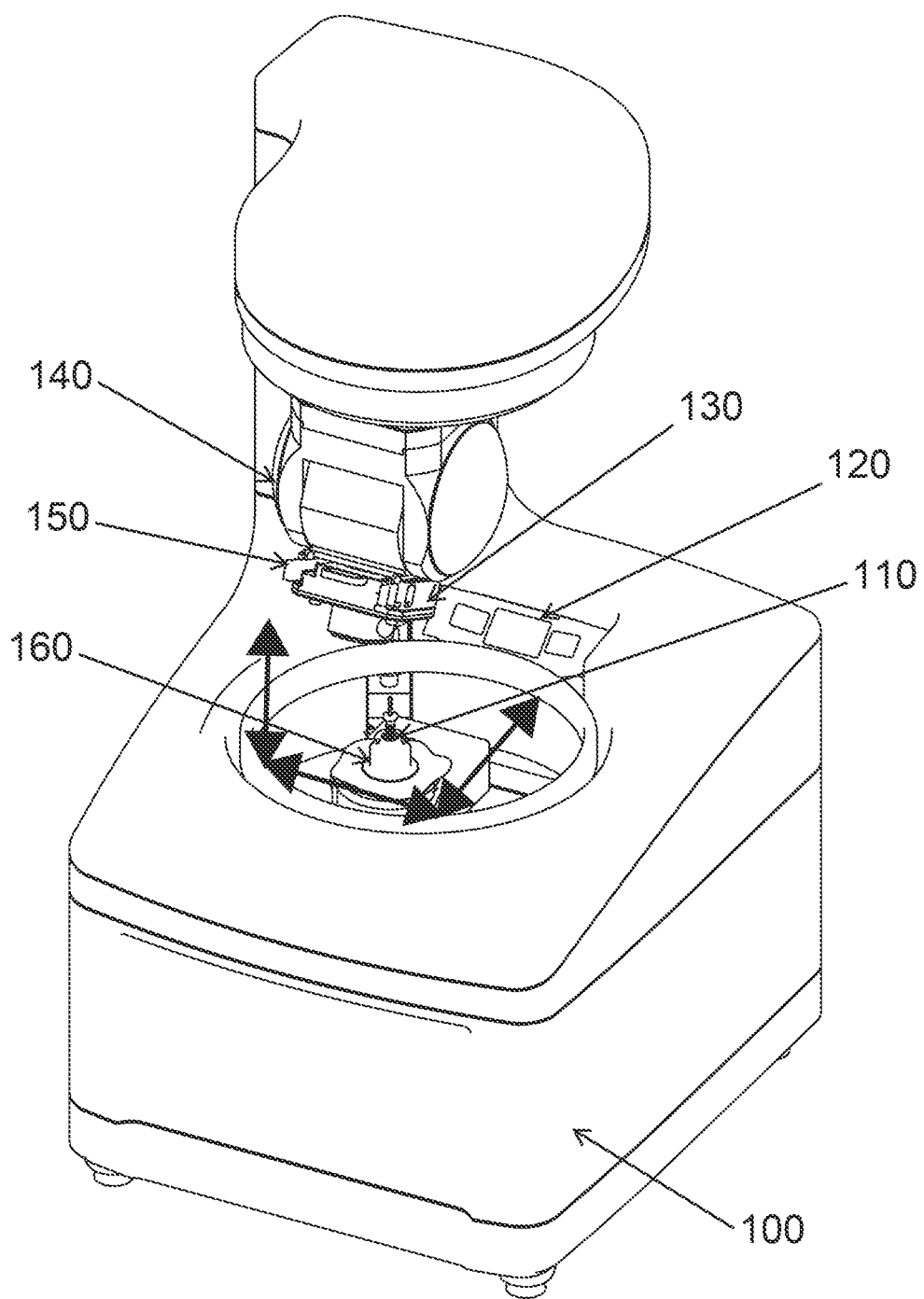
FIG. 1 shows a production apparatus for use with an embodiment of the invention.

FIG. 1 shows a production apparatus 100 for use with an embodiment of the invention. The production apparatus 100 is configured to modify an impression of a surgical site (taken using the mouldable material carrier described herein) to produce a surgical guide. The production apparatus 100 is intended to be used within the operating room and situated next to the operating table.

The production apparatus 100 comprises a coupling section 160 configured to couple to a replaceable cutting attachment 110 and a mounting point 130, upon which a surgical guide carrier 150 may be mounted. The surgical guide carrier 150 is a removable mounting point for a surgical guide. The surgical guide carrier 150 is configured to secure an impression of a surgical site to the production apparatus 100 in a predefined position and orientation. The production apparatus 100 includes a scanner 120 for scanning a surface of the impression.

The production apparatus 100 is configured to scan the surface of the impression and compare this to a stored medical scan of the patient's anatomy. This medical scan may be an MRI scan, a CT scan, or any other scan capable of recording the patient's anatomy. The scan of the surface of the impression may be an optical scan or any other scan capable of measuring the geometry of the surface of the impression.

The production apparatus 100 is configured to register the impression to the anatomical features of the patient. This allows the production apparatus 100 to determine where surgical guide holes need to be drilled into the impression in order to produce a surgical guide according to a predetermined surgical plan.

The registration process allows the production apparatus 100 to calibrate itself with respect to the impression in order to ensure that guide holes are drilled in the correct position.

The cutting attachment 110 can be releasably mounted on to the production apparatus 100 at the coupling section 160 of the production apparatus 100. The coupling section 160 is connected to a motor for driving the cutting attachment 110.

The surgical guide carrier 150 can be releasably mounted upon a mounting point 130 on the production apparatus 100. The mounting point 130 is attached to a gimbal 140 of the production apparatus 100. The gimbal 140 forms part of a rotation mechanism that includes a motor that is configured to rotate the mounting point, and the surgical guide carrier 150, about a tilt axis running parallel to the ground (along the horizontal plane).

The rotation mechanism further comprises a yaw axis drive member, located on the gimbal. The yaw axis drive member is configured to mate with a yaw axis keyway in the surgical guide carrier 150 to rotate a rotatable section of the surgical guide carrier about a yaw axis running radially from the tilt axis.

The rotation mechanism therefore allows the production apparatus 100 to rotate a surgical guide carrier 150 about the tilt axis, and rotate the impression of the surgical site about the yaw axis, to move the impression into the correct orientation to allow a surgical guide hole to be formed along the correct line.

The gimbal 140 also allows the production apparatus 100 to rotate the surgical guide carrier 150 into a forward orientation to allow the surgical guide to be coupled and uncoupled from the production apparatus 100 and to rotate the surgical guide carrier 150 to a backward orientation to allow the production apparatus 100 to scan the surface of an impression of the surgical site to produce a plan for modifying the impression.

The coupling section 160 is located on a movable arm. The production apparatus is configured to be able to move the movable arm along three orthogonal directions, x, y and z (shown in FIG. 1). This allows the production apparatus 100 to position the cutting attachment 110 in the correct position and to drive the cutting attachment 110 into the impression to produce a surgical guide hole within the impression at the required location.

The mounting point 130 is located above the coupling section 160 so that, when the impression is being modified, debris from the impression falls downwards, away from the impression and towards the cutting element.

The general process of scanning and modifying an impression of the surgical site using a production apparatus is discussed in more detail in WO 2015/075423 A1 (the entirety of which is hereby incorporated by reference).

The embodiments described herein are generally directed towards a mouldable material carrier (shown in FIGS. 2-11) and, in particular, a mouldable material carrier for use with a production apparatus such as the example shown in FIG. 1. The mouldable material carrier allows an impression of a surgical site to be taken and forms part of the surgical guide when the impression has been modified.

In accordance with the embodiments described herein, the mouldable material carrier is configured to contain the mouldable material within the carrier via a flexible sheet, through which the impression may be taken. This allows an impression of a surgical site to be taken without the mouldable material coming into contact with the surgical site. This will prevent mouldable material from unnecessarily being deposited on the surgical site and prevent contamination. Without this flexible sheet, mouldable material can be deposited within the surgical site and may require removing before the surgery can be completed.

Furthermore, the flexible sheet ensures that the mouldable material is compressed during as the impression is taken. This ensures that a more effective impression is taken that fits the surgical site more accurately and is able to be registered with scans of the surgical site more effectively. Registration software often makes use of edge detection to detect the orientation of the impression and match this up with the surgical plan (via preoperative scans of the surgical site). The inventors have found that impressions taken with unconfined mouldable material can result in the mouldable material being urged peripherally as the impression is taken. This can result in a messy and jagged outer shape. This not only makes it more difficult for the production apparatus to register the impression with the surgical plan, but also results in a less secure fit around a surgical site. By confining the mouldable material within a flexible sheet, the mouldable material is prevented from escaping the immediate vicinity of the surgical site, and is compressed around the surgical site to form a clearer and more secure fit around the surgical site.

Additionally, the flexible sheet allows for more mouldable material to be used effectively. The flexible sheet confines the mouldable material within a volume inside the mouldable material carrier. Therefore more mouldable material can be used without it detaching from the mouldable carrier during use. By allowing a greater amount of mouldable material to be used, this also provides a better fit around the surgical site, especially for edge surfaces.

To aid in the insertion of mouldable material in to the device, a mouldable material dispenser may be provided (shown in FIGS. 8 and 9) in the general form of a syringe. This can be used to dispense mouldable material into the mouldable material carrier through an inlet within the mouldable material carrier.

An impression of a surgical site can be taken using mouldable material dispensed into the mouldable material carrier. Once the impression has been taken, the mouldable material carrier can then be coupled to the production apparatus 100 via the surgical guide carrier 150 when the surgical guide carrier 150 is mounted on the production apparatus 100. The production apparatus 100 can then scan the impression of the surgical site and modify the impression with the cutting attachment 110.

Preparation of the production apparatus 100 can be carried out by a sterile scrub nurse. The individual accessories can be supplied either double pouched or in a blister pack arrangement. The circulating nurse can then open the outer packaging allowing the sterile accessories to be transferred aseptically for use by the scrub nurse.

Figure 2:
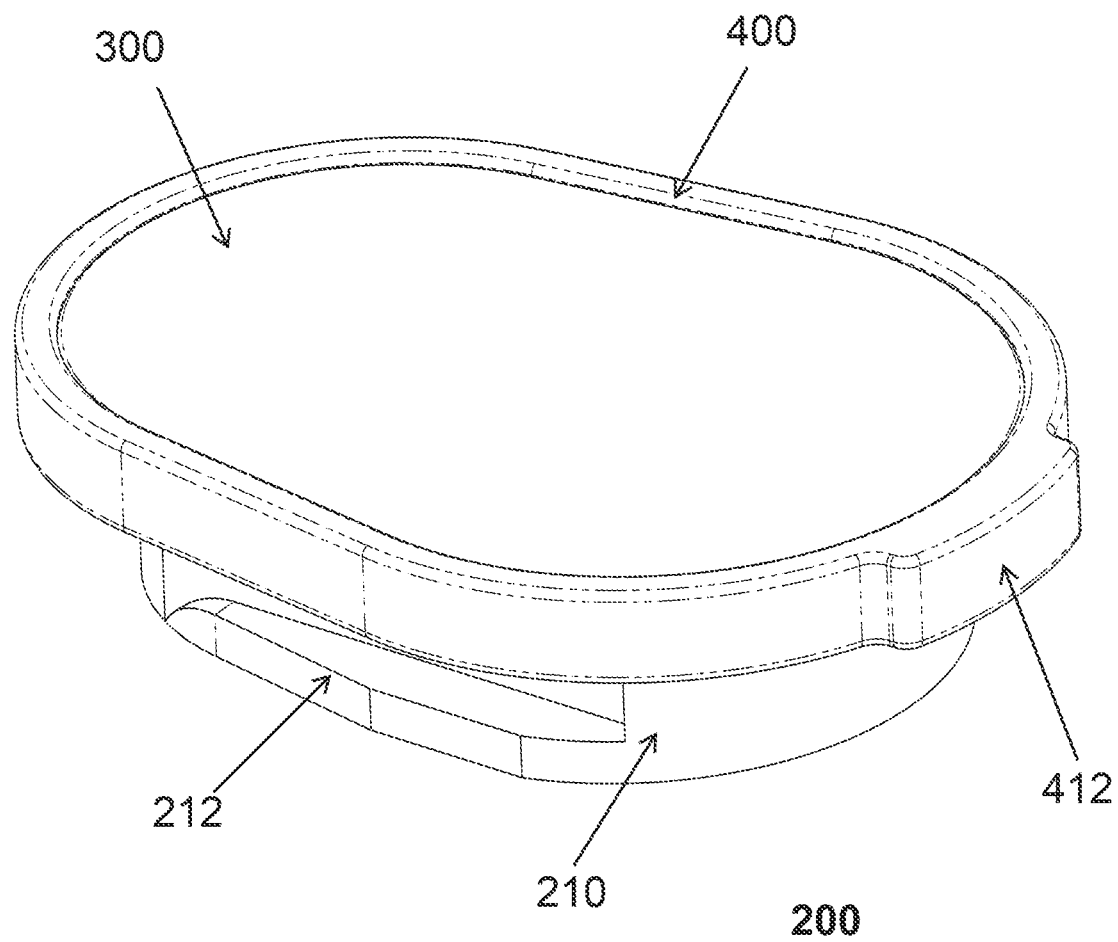
FIG. 2 shows a mouldable material carrier in accordance with an embodiment of the invention.

FIG. 2 shows a mouldable material carrier 200 in accordance with an embodiment of the invention. The mouldable material carrier 200 comprises a base 210, a retaining ring 400 and a flexible sheet 300. The retaining ring 400 is configured to secure the flexible sheet 300 to the base 210. The mouldable material carrier 200 includes an inlet (shown in FIG. 3) through which mouldable material may be injected into the mouldable material carrier 200. Once injected, the mouldable material sits between the flexible sheet 300 and the base 210.

The flexible sheet 300 acts as a barrier to prevent mouldable material from escaping into the surgical site whilst an impression is taken, whilst being sufficiently flexible to allow an accurate impression of the surgical site to be taken. Advantageously, the flexible sheet 300 may be elastic to help compact the mouldable material and form a more accurate impression. The flexible sheet may have a Young's modulus of between 0.1 and 0.01 GPa, although other levels of elasticity may be used.

The retaining ring 400 is in the form of a ring that encircles the periphery of the base 210. The retaining ring 400 therefore secures the flexible sheet 300 around the edge of the base 210. The retaining ring 400 secures the flexible sheet 300 along a continuous path thereby forming a seal between the flexible sheet 300 and the base 210. By seal, it is meant that the flexible sheet 300 is secured against the base 210 such that mouldable material may not pass between the flexible sheet 300 and the base 210. The seal need not be airtight or watertight.

The retaining ring 400 releasably secures the flexible sheet 300 to the base 210 such that the flexible sheet 300 may be removed from the base 210. The retaining ring 400 comprises a finger release tab 412 to provide a handle or lever that assists the user in releasing the retaining ring 400 from the base 210.

The base 210 comprises a coupling portion 212. In the present embodiment, the coupling portion 212 is in the form of two channels passing along side walls of the base 210. The coupling portion 212 is configured to couple with the production apparatus 100 (in this case, via corresponding grooves in the surgical guide carrier 150) in a predetermined position and orientation. This ensures that, once the mouldable material carrier 200 has been registered with the production apparatus 100, registration between the mouldable material carrier 200 and the production apparatus 100 is maintained regardless of whether the mouldable material carrier 200 is subsequently decoupled and re-coupled with the production apparatus 100.

Figure 3:
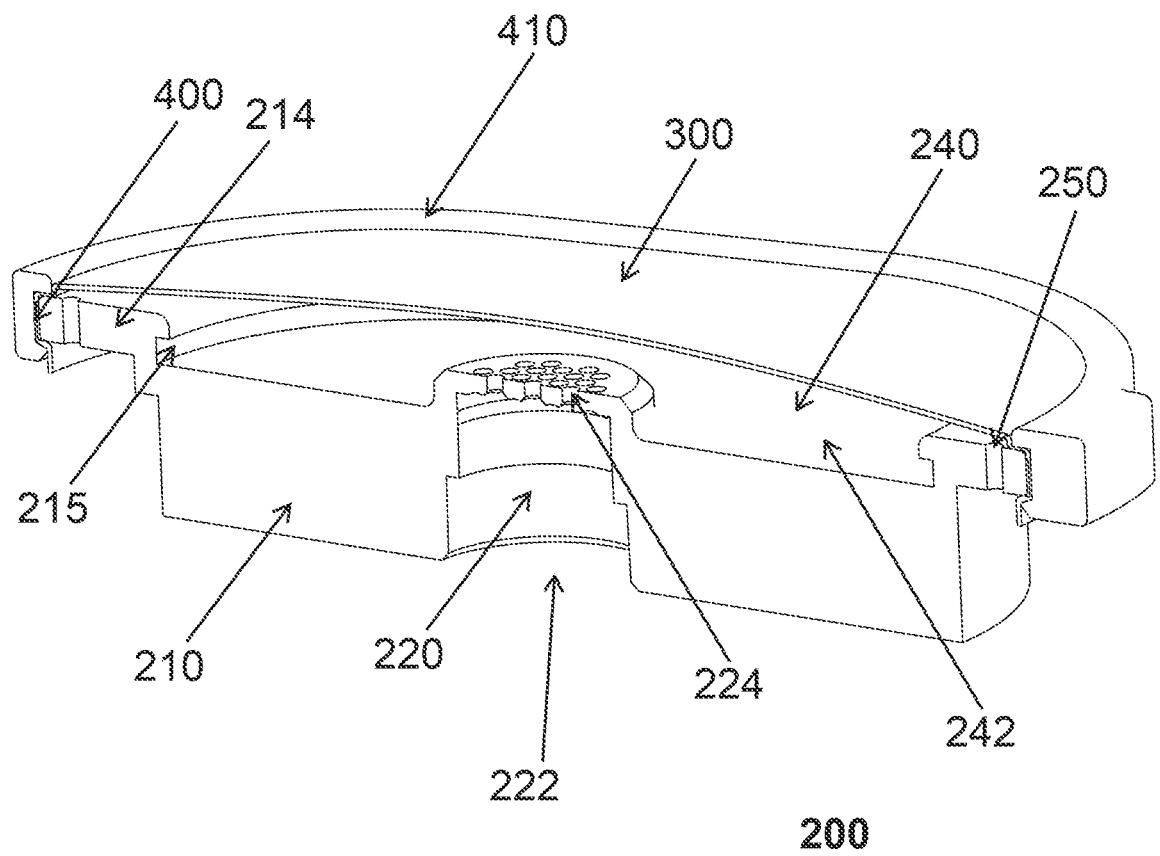
FIG. 3 shows a cross-sectional view of the mouldable material carrier of FIG. 2.

FIG. 3 shows a cross-sectional view of the mouldable material carrier 200 of FIG. 2. The mouldable material carrier 200 is configured to secure the flexible sheet 300 to the base 210 of the mouldable material carrier and to receive mouldable material in such a way that mouldable material is confined within a volume 240 defined by the flexible sheet 300 and the base 210.

A channel 220 is formed within the centre of the base 210, passing through the base 210 between an inlet 222 and an outlet 224. The inlet 222 is located on a rear side of the base 210, opposite to a front side of the base 210 over which the flexible sheet 300 is secured. The outlet 224 is located on the front side of the base 210. The volume 240 is defined by the space between the front side of the base 210 and the flexible sheet 300.

The base 210 comprises a peripheral wall that encircles the outlet 224. The peripheral wall is located at the periphery of the front side, and defines a cavity 242 within the front side of the base 210. The cavity is an indent within the front side of the base, formed by the side wall and a bottom of the cavity. The outlet 224 is located in the bottom of the cavity.

A rim is formed around the outside of the peripheral wall in the form of a flange 214. This extends around the periphery of the base 210. The flange 214 is located on the front side of the base and extends radially away from the outlet 224. As the flange 214 is located at the top end of the peripheral wall, the flange 214 is raised above the base of the cavity 242.

An undercut is formed in the inner side of the peripheral wall. The undercut is defined between the bottom of the cavity 242 and a lip 215 that radially protrudes from the inner side of the peripheral towards the centre of the cavity 242. The lip 215 therefore forms a protruding portion that protrudes in to the cavity 242. That is, the direction of protrusion converges towards the outlet 224. The lip 215 is positioned above the bottom of the cavity 242 such that is does not contact the front side of the base. The undercut provides a key between the mouldable material and the mould. As the mouldable material is urged into the cavity 242 to fill the cavity 242, it also fills the undercut. When the mouldable material sets, the lip 215 therefore couples to the mouldable material to prevent the mouldable material from detaching from the mouldable material carrier 200.

The outlet 224 is located within an upwardly protruding plateau that is raised above the bottom of the cavity 242 such that it protrudes into the cavity 242. This upward protrusion helps to form the material into a dome shape such that it is shaped to fit well within a surgical site. The opening of the outlet 224 is composed of holes provided via a grating. The holes are evenly distributed in a honeycomb configuration. This helps to provide an even distribution of mouldable material.

The holes, having reduced dimensions relative to the channel 220, allow mouldable material to be urged into the cavity (e.g. via a syringe) but resist the mouldable material escaping the cavity. The holes therefore act as a simple one-way valve without requiring any movable parts or more complex mechanisms. This means that the base 210 can be easily manufactured (e.g. via injection moulding or additive manufacturing) in a single step. Furthermore, by avoiding the use of a more complex valve mechanism, the base 210 is more robust and suitable for modification to produce a surgical guide (e.g. via the drilling or cutting of guide holes or guide channels). If a valve mechanism with moving parts were to be provided, this would run the risk of shattering during modification and could result in excess debris that could become lodged within the surgical site.

The flexible sheet 300 is secured to the outer periphery of the flange 214 of the base 210. The flexible sheet 300 is secured to the flange 214 by a securing portion 410 forming part of the retaining ring 400. The securing portion 410 comprises a groove within the inward face of the retaining ring 400 that is configured to clip over the flange 214. By clipping the retaining ring 400 over the outer edge of the base 210 (over the flange 214), the flexible sheet 300 is clamped between the retaining ring 400 and the base 210. In this arrangement, the flexible sheet 300 is wrapped around the edges of the flange 214 of the base 210 to form a seal across the front side of the base 210. The retaining ring 400 clamps the flexible sheet 300 to the sides and edges of the flange 214 such that the flexible sheet 300 covers the entire front side of the base 210.

Air holes 250 are formed through the flange 214 from a front side of the flange to a rear side of the flange. The air holes 250 are evenly distributed around the whole circumference of the flange 214. The air holes 250 go through the entire thickness of the flange 214 such that air in the volume 240 may pass through the air holes 250. This allows air to escape the volume 240 whilst mouldable material is urged into the volume 240. By providing the air holes 250 within the flange 214, rather than through the main body of the base 210, the air holes 250 are located towards the periphery of the base 210. By providing the air holes 250 towards the periphery of the base 210, air is more effectively urged out of the volume as the mouldable material moves from the centrally located channel outwards towards the air holes 250. The air holes 250 are sized similarly to the holes in the outlet 224, in that they are large enough to allow air to pass but are small enough to resist mouldable material passing.

During use, mouldable material may be inserted into the volume 240 through inlet 222. Mouldable material will then travel down the channel 220 and be released through the outlet 224 to be deposited into the volume 240.

As more mouldable material is inserted into the volume 240 of the mouldable material carrier 200, the mouldable material will occupy more space of the volume 240 that is defined by the base 210 and flexible sheet 300. The mouldable material is contained within the flexible sheet. This means that the mouldable material is contained within the mouldable material carrier 200. This prevents the mouldable material from spreading to unwanted areas, such as the surgical site.

The process of taking an impression using this mouldable material carrier requires less user skill due to easy manipulation of the carrier since it will not spread the material within the surgical site. Furthermore, the mouldable material carrier provides an impression with an improved quality of mould surface since the mouldable material does not touch the surgical site and interact with any fluids. This provides a much smoother surface which better represents the underlying surgical site (such as the surface of underlying bone within the surgical site).

What is more, in the present embodiment the flexible sheet 300 is elastic. This means that the flexible sheet 300 provides a compressive force to the mouldable material. At the periphery, the surface pressure of the membrane provides a force perpendicular to the applied force (the direction in which the impression is being taken) to more accurately capture surfaces at the edge. This is because the mouldable material is retained and compressed at the edge. Accordingly, instead of spreading out and potentially detaching from the main body of the impression, the mouldable material at the edges is retained and, in some cases, wraps around the edge of the body part from which the impression is being taken. This helps to provide a more accurate registration with said body part in the surgical site. Not only does this make it easier for the surface of the impression to be matched to scans of the patient to allow a more accurate modification plan for modifying the impression to produce a surgical guide to be produced, but also ensures that the impression forms a more secure fit with the surgical site.

In addition to the above, as the mouldable material is contained within the mouldable material carrier 200 by the flexible sheet 300, the mouldable material carrier 200 may be used to take impressions at a variety of angles relative to the bottom of the cavity without the risk of the mouldable material detaching from the mouldable material carrier 200. That is, an impression need not be taken by urging the mouldable material carrier 200 against a surgical site in a direction perpendicular to the front side of the mouldable material carrier 200. Instead, the impression may be taken by urging the mouldable material carrier 200 against a surgical site in a variety of angles whilst the flexible sheet 300 acts to retain the mouldable material within the mouldable material carrier 200.

As the flexible sheet 300 is secured to the base 210, the user is able to use a larger quantity of mouldable material without risking it detaching from the mouldable material carrier during use. Using more mouldable material provides the advantage of the mouldable material carrier 200 wrapping around a larger portion of the surgical site, which allows more surface data to be registered. It also provides the advantage of getting more accurate impressions of edge surfaces for smaller surgical sites After an impression of a surgical site is taken by the mouldable material carrier 200, the mouldable material inside the volume 240 may harden to form a set impression of the surgical site. This allows the impression to be modified by a production apparatus 100 to produce a surgical guide without significantly deforming the impression. The modified impression can then be fitted back in the surgical site and used as a surgical guide.

In the present embodiment, the base 210 may be substantially rigid. It may be formed of a rigid, biocompatible material, such as plastic. Having said this, the base 210 need not be completely rigid. The base 210 could have some flexibility whilst still achieving the main functions of mouldable material carrier 200 of containing the mouldable material and providing a carrier for handling the material and coupling to the production apparatus 100. The base 210 may be rigid enough to not alter the impression of the surgical site provide by the mouldable material carrier 200 but still have some flexibility to bend during use.

The flexible sheet 300 may be composed of biocompatible materials. In particular, the flexible sheet 300 may be of material that does not cause a damaging effect to the tissue within the surgical site. In particular, but without limitation, examples of potential materials for the flexible sheet include neoprene, latex, polysioprene and nitrile polymers.

Figure 4:
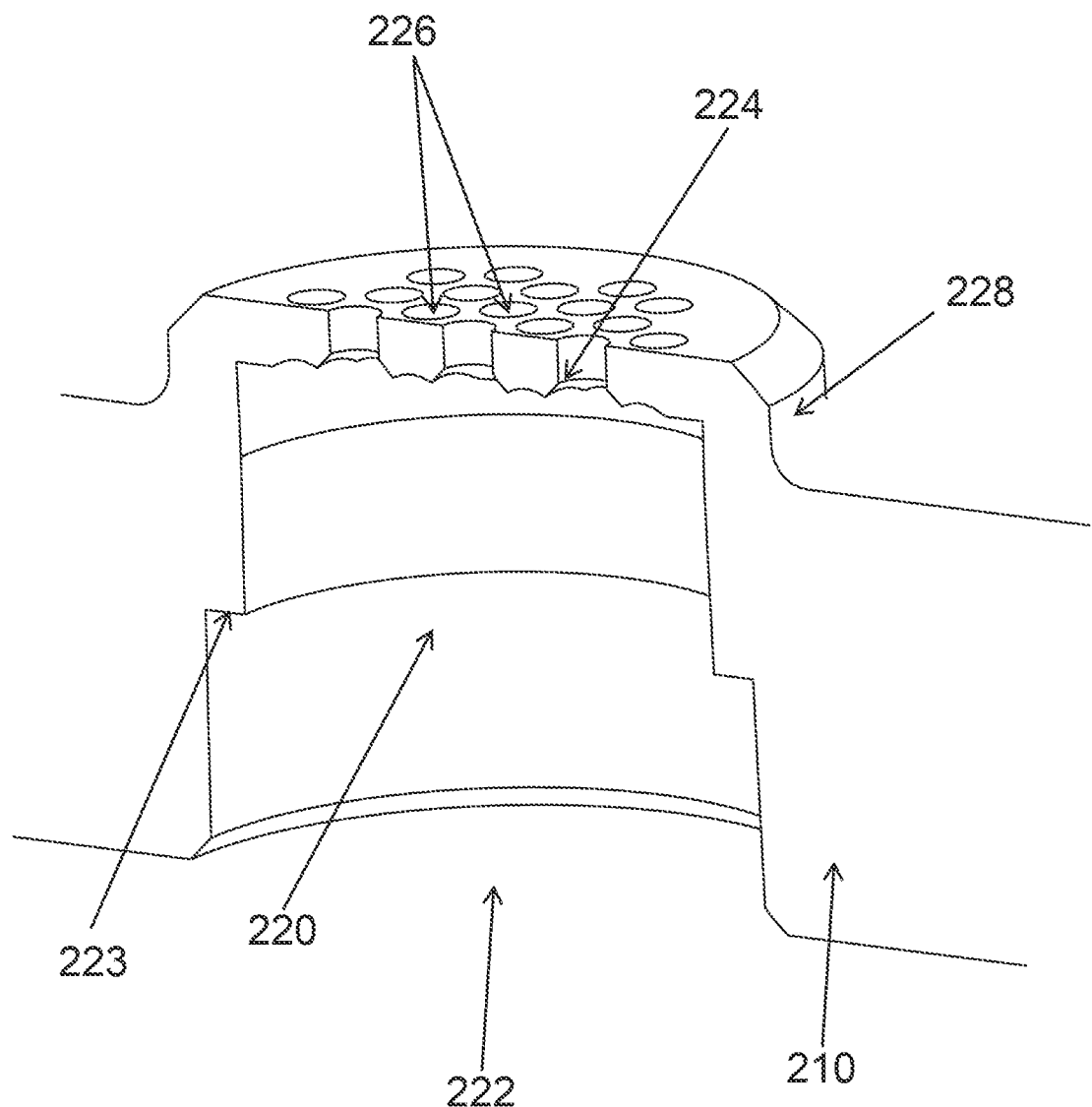
FIG. 4 shows a close up view of an inlet channel of the mouldable material carrier of FIG. 3.

FIG. 4 shows a close up view of the channel 220 of the mouldable material carrier 200 of FIG. 3. The channel 220 is a cylindrical channel that formed within the centre of the base 210, passing through the base 210 between the inlet 222 and the outlet 224. The inlet 222 is located on a rear side of the base 210, opposite to a front side of the base 210 over which the flexible sheet 300 is secured. The outlet 224 is located on the front side of the base 210.

The outlet 224 comprises a plurality of outlet holes 226 on its surface, wherein the surface is elevated by a raised portion 228. The outlet 224 is formed in a raised surface above the front side of the base 210. The outlet holes 226 are evenly distributed in a honeycomb configuration on the raised surface. The inlet 222 is a hole connected to the outlet 224 in fluid communication through the channel 220. The inlet 222 is bevelled around its periphery.

The channel 220 that connects the inlet 222 and outlet 224 comprises an abutment 223 along its length such that the diameter of the outlet 224 is less than the diameter of the inlet. The abutment 223 is a reduction in the width of the channel along the channel 220 from the inlet 222 to the outlet 224.

The abutment 223 is formed at the end of a cylindrical channel that connects to the outlet 224. This cylindrical channel is narrower than the cylindrical channel that is open via the inlet 222. Mouldable material may be inserted into the volume 240 of the mouldable material carrier 200 via a mouldable material dispenser, usually in the general form of a syringe (shown in FIGS. 8 and 9). The abutment 223 restricts a user from over-inserting such a mouldable material dispenser into the channel 220. This protects the outlet 224, wherein the grating forming the outlet holes 226 may be prone to damage from over-insertion of the mouldable material dispenser. Accordingly, the abutment 223 is configured to prevent a syringe having a diameter similar to that of the inlet 222 from being inserted all the way through the channel 220. The abutment 223 also helps to ensure that the mouldable material is directed towards the outlet 224 rather than passing back through the inlet 222.

The bevelled portion of the inlet 222 also reduces the risk of a mouldable material dispenser damaging the mouldable material carrier 200. The bevelled portion of the inlet 222 assists a user in guiding the mouldable material dispenser into the channel 220. Since the mouldable material carrier 200 may be used as the surgical guide itself, it is important that there are no structural defects present in mouldable material carrier that may hinder that accuracy of the registration, modification or surgical guide placement.

When mouldable material is inserted into inlet 222 of the mouldable material carrier 200 through the channel 220, mouldable material is extruded through the outlet holes 226. If enough mouldable material accumulates inside the volume 240 (shown in FIG. 3), the flexible sheet 300 will exert a reactionary force on the mouldable material that is inside the volume 240. The mouldable material inside the volume 240 will consequently be urged against the outlet 224.

The outlet holes 226 are therefore of reduced dimensions relative to the channel 220 to resist the mouldable material from escaping the volume 240 through the channel after the mouldable material has been urged into the volume 240. This creates a high pressure requirement for mouldable material to pass through the grating of outlet holes 226, in effect causing the grating to act as a one-way valve. Specifically, the high pressure requirement provides the advantage of allowing mouldable material to be deliberately urged into the volume 240 by a user but effectively resists the low pressure from the reactionary force from the flexible sheet 300. The grating of the outlet 224 also resists the mouldable material from escaping the volume 240 when an impression is taken by a user.

The high pressure requirement is large enough to resist the reactionary force from the surgical site when the mouldable material carrier 200 is urged against the surgical site to form an impression. The outlet 224 acts as a one-way valve without requiring a mechanism with moving parts. This allows the mouldable material carrier 200 to be manufactured in a simpler and less expensive process. The mouldable material carrier 200 is also configured to be modified by the production apparatus 100 to form a surgical guide. Having multiple features integrated in the single base 210 of the mouldable material carrier 200 provides safer and more effective modification. The absence of moving parts reduces the risk of shrapnel or debris detaching from the base 210 during modification.

Advantageously, the outlet holes 226 have an even distribution across the outlet 224. The even distribution provides an even distribution of mouldable material within the cavity 242 as the mouldable material is extruded through the outlet holes 226.

Figure 5:
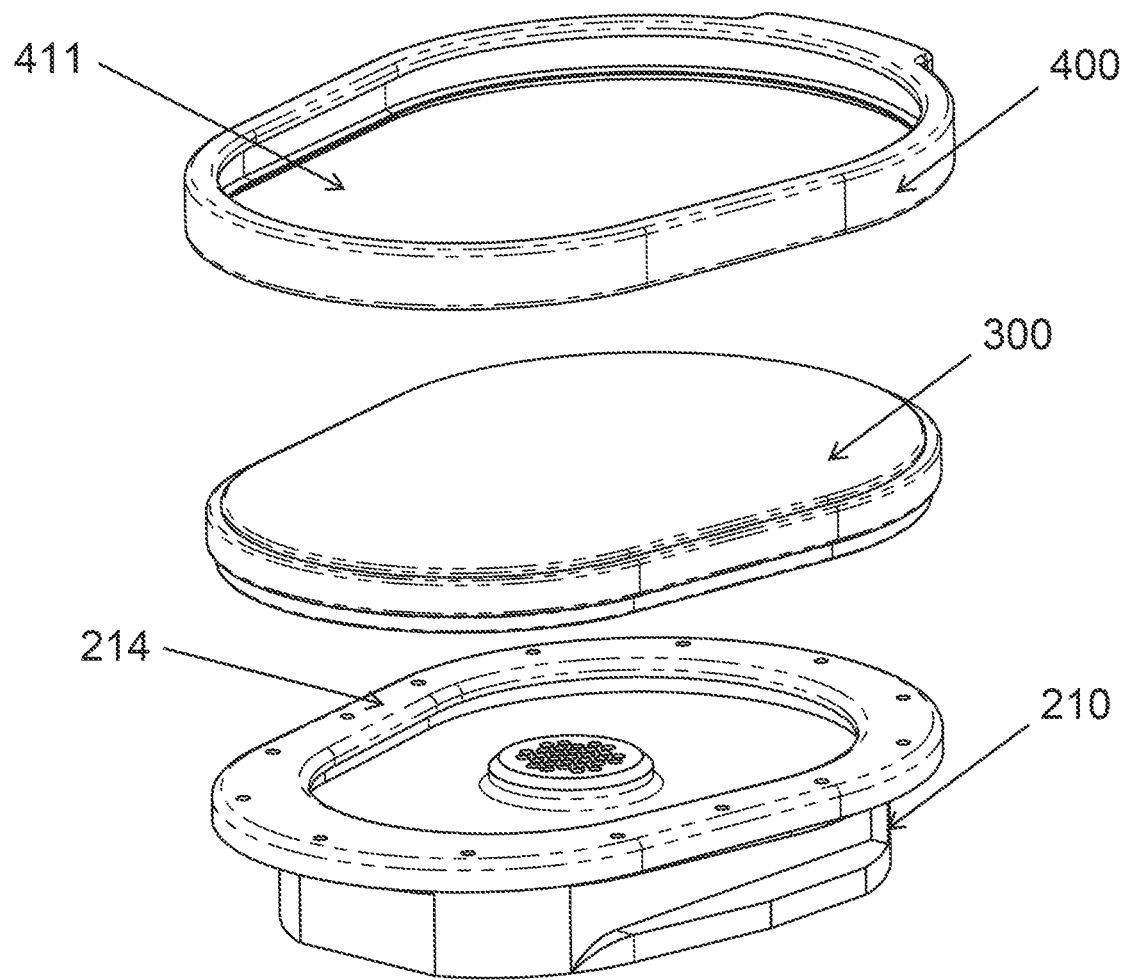
FIG. 5 shows a perspective exploded view of the mouldable material carrier.

FIG. 5 shows a perspective exploded view of the mouldable material carrier 200. The exploded view shows three separable sections of the mouldable material carrier 200: base 210, flexible sheet 300 and retaining ring 400. The peripheries of the three compartments have similar cross-sections so that they are configured to align with each other. The cross-section in this particular embodiment is an oval shape. The mouldable material carrier 200 is assembled by placing the flexible sheet 300 over the front side of the base, wrapping the flexible sheet 300 around the flange 214. The flexible sheet 300 is then secured by the clipping the retaining ring 400 over the flange 214 securing portion 410.

The retaining ring 400 of the securing portion 410 comprises an opening 411 through which the flexible sheet is exposed when secured to allow an impression to be taken through the flexible sheet.

The mouldable material carrier described with reference to all the figures has a base 210, flexible sheet 300 and retaining ring 400 that have similar cross-sections, such that the flexible sheet 300 fits around the base 210 and the retaining ring 400 fits around the flexible sheet 300. There are many different arrangements that can allow the three sections to be assembled together. For instance, the mouldable material carrier 200 can still carry out all the functions described above if the flexible sheet 300 had a square or circular shaped periphery. The shape of the mouldable material carrier 200, or at least the cross-section of the mouldable material carrier 200, may therefore be adapted for the particular use (e.g. to conform to the shape of a surgical site).

Figure 6:
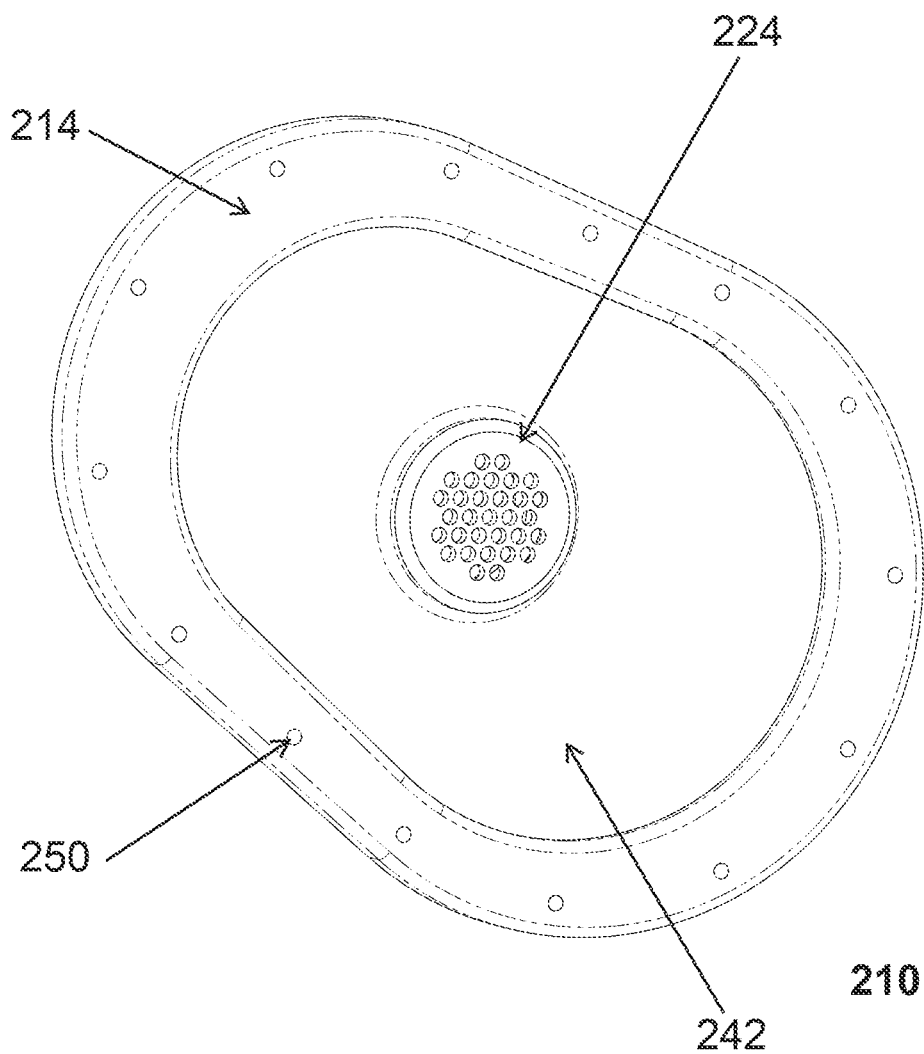
FIG. 6 shows a plan view of the base.

FIG. 6 shows a plan view of the base 210. The outlet 224 is located at the centre of the cross-section of the front surface of the base 210, within the cavity 242. The flange 214 forms a ring around the periphery of the base 210. The air holes are evenly distributed along the flange 214.

Figure 7:
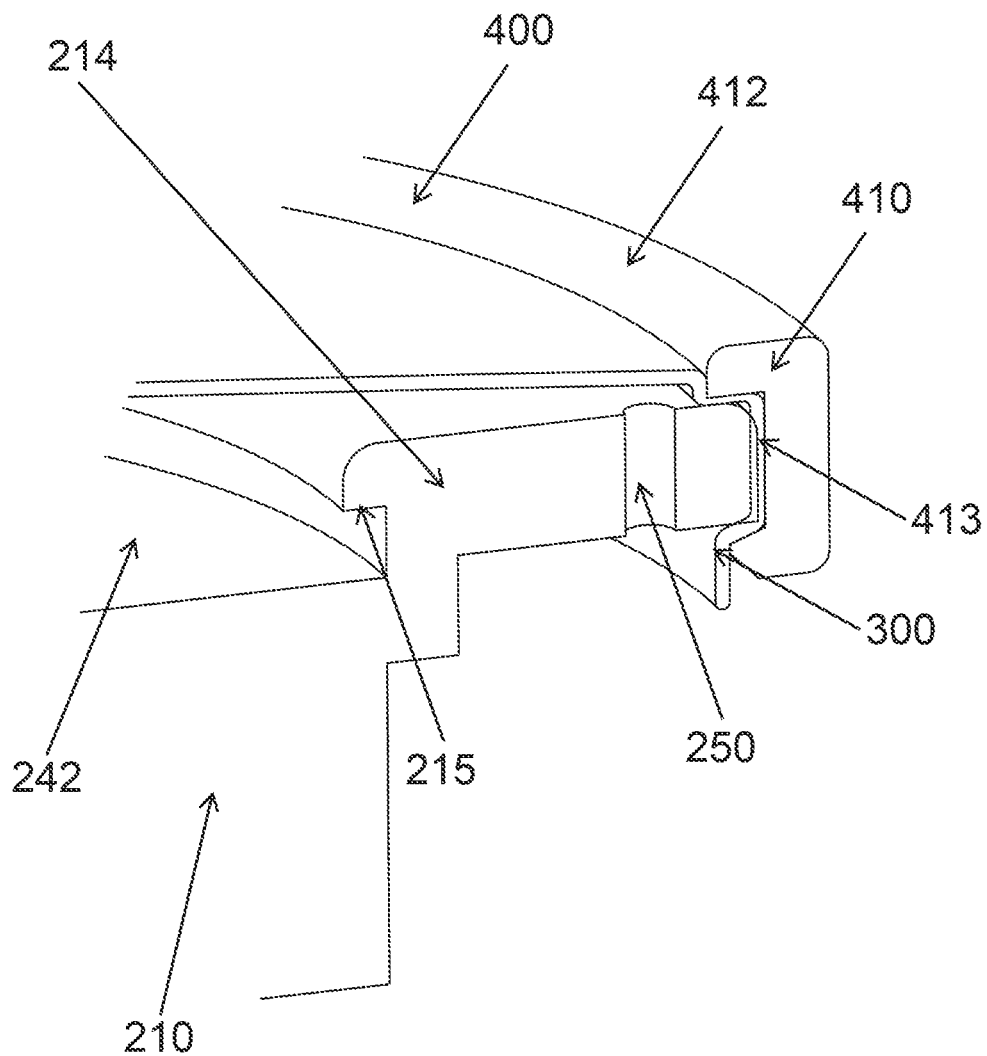
FIG. 7 shows a close up cross-sectional view of a rim of the mouldable material carrier of FIG. 6.

FIG. 7 shows a close up cross-sectional view of a rim securing portion 410 of the mouldable material carrier 200 of FIG. 3. The flange 214 laterally extends from the base 210, radially from the centre, and above the bottom of the cavity 242. The flange 214 has equally spaced air holes 250 such that air can pass from the cavity 242 through the air holes 250. The base 210 further comprises a lip 215 which extends from the inner periphery of the flange 214. The lip 215 is a protruding portion that protrudes in to the cavity 242; the direction of protrusion converges towards the outlet 224. The lip 215 is positioned above the bottom of the cavity 242 such that is does not contact the front side of the base and instead forms an undercut.

The flexible sheet 300 is secured to the flange 214 of base 210 by the retaining ring 400 via the securing portion 410. The securing portion 410 is in the form of a groove 413 (or channel) of similar dimensions to the flange 214 and configured to fit over the flange 214 and provide an interference fit between the flange 214 and the securing portion 410.

The flexible sheet 300 wraps around the edges of the flange 214. The retaining ring 400 is secured onto the base 210 by clipping onto the edges of the flange 214 over flexible sheet 300. The retaining ring 400 clips over the edges of the flange 214, by the groove 413 clamping the flexible sheet 300 onto around the periphery of the flange 214. To achieve this, the retaining ring 400 is resiliently deformable.

A finger release tab 412 is provided as a lateral protrusion from periphery of the retaining ring 400. This acts as a handle or lever to allow the user to get purchase on the retaining ring to release the securing portion 410 from the base 210. The retaining ring 400 therefore releasably secures the flexible sheet 300 to the base 210.

In use, the flexible sheet 300 is secured to the base 210 when an impression of a surgical site is being taken and the flexible sheet 300 is secured to the base 210 when the mouldable material carrier 200 is being filled with mouldable material.

The securing portion 410 may be released to detach the flexible sheet 300 from the base 210. The flexible sheet 300 may be detached from the mouldable material carrier 200 so that its surface can be more accurately registered by the production apparatus 100. Furthermore, the removal of the flexible sheet 300 ensures that that it does not interfere with the modification of the impression, and provides a more secure fit between the impression and the surgical site.

In one embodiment, the flexible sheet 300 comprised a pull tab (not shown) extending at an edge of the flexible sheet 300 to aid the user in detaching the flexible sheet 300 from the mouldable material carrier 200.

The cavity 242 will contain air before mouldable material is inserted into the mouldable material carrier 200. To obtain an accurate impression of the surgical site, it is important to fill the cavity 242 with enough mouldable material and also to remove the air that was initially present before use. If too much air is present within the cavity 242, registration of the impression will include errors due to the additional dimensions of the initial air and/or air bubbles present within the inserted mouldable material. The registration could also include errors due to reduced dimensions. For example, whilst a user waits for the mouldable material inside the cavity 242 to harden, the initial excess air may escape the mouldable material carrier during the hardening process. This will reduce the volume 240 defined by the flexible sheet 300 and base 210 and alter the impression of the surgical site, hindering the accuracy of the impression of the surgical site.

The air holes 250 allow the aforementioned air to escape from the cavity 242 whilst the mouldable material carrier 200 is being filled with mouldable material and when an impression is being taken. As mouldable material enters the cavity 242 via the outlet 224, the mouldable material will occupy more space in the volume 240 defined by the base 210 and flexible sheet 300. As more mouldable material enters the cavity 242, air will be urged out of the air holes 250. The air will therefore leave the mouldable material carrier 200 as the mouldable material displaces the air. When an impression is being taken, the mouldable material inside the cavity 242 will be compressed and expand outwards. This can lead to additional displacement of air with the mouldable material, which will lead a more accurate impression of the surgical site.

The air holes 250 are of reduced dimensions relative to the channel 220 to resist the mouldable material from escaping the volume 240 through the air holes 250 whilst an impression is being taken. This creates a high pressure requirement for mouldable material to pass through the air holes 250, in effect causing the air holes 250 to allow air to pass but preventing the passage of mouldable material.

The air holes 250 are equally spaced around the rim. Specifically, the air holes 250 are distributed evenly around the flange 214. This locates the air holes 250 towards the periphery of the base to ensure that air is not accumulated at specific regions inside the volume 240 and to ensure that the air is effectively removed from the volume 240. Having said this, the air holes 250 need not be located within the flange 214, and may pass through the main body of the base 210 in addition to, or instead of, passing through the flange 214.

The lip 215 helps couple the mouldable material to the mouldable material carrier 200 and helps resist the removal of the mouldable material from the cavity after the mouldable material has been urged into the cavity 242. After enough mouldable material has been urged into the cavity 242, the mouldable material will cover the bottom of the cavity (defined by the front side of the base 210) and the sides of the cavity (defined by the peripheral wall). Since an impression of a surgical site is taken by placing the flexible sheet on a surgical site, the mouldable material carrier 200 may be used in various orientations. The peripheral wall resists transverse movement of the mouldable material whilst it is present in the cavity 242. The lip 215 resists longitudinal movement of the mouldable material whilst it is present in the cavity 242. For instance, when the mouldable material carrier 200 is orientated such that the flexible sheet 300 is facing the ground, the lip 215 withstands the weight of the mouldable material inside the cavity 242 to prevent the mouldable material from falling out of the mouldable material carrier 200.

It is important to provide a secure means of coupling the mouldable material to the mouldable material carrier. This resists excessive movement of the mouldable material inside the mouldable material carrier 200. This is important as it could alter the impression of the surgical site during use and could result in inaccurate modification of the impression and/or undesirable movement of the surgical guide during surgery.

Preferably, the flexible sheet 300 may be elastic such that is provides a compressive force to the mouldable material and helps to tightly confine the mouldable material inside the volume 240. Additionally, it is important that the flexible sheet 300 is sufficiently flexible to allow an accurate impression This allows the flexible sheet 300 to be removed after the impression has been formed (and the mouldable material has set) so that it does not interfere with the modification of the impression, and to provide a more secure fit between the impression and the surgical site to be taken through the flexible sheet 300.

Figure 8:
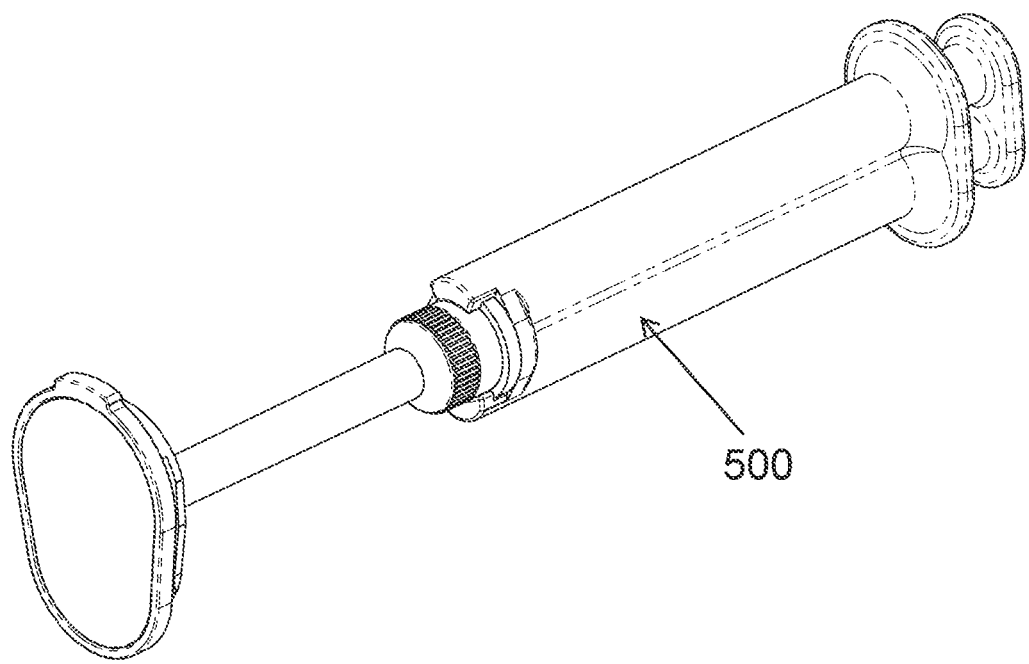
FIG. 8 shows a perspective view of the mouldable material carrier in use with a syringe.

FIG. 8 shows a perspective view of the mouldable material carrier 200 in use with a mouldable material dispenser 500. As discussed above, an inlet 222 is formed in the rear side of the base 210 of the mouldable material carrier 200. The inlet 222 and outlet 224 connected by a channel 220, having an abutment 223 such that its diameter reduces as it passes from the inlet 222 to the outlet 224. The abutment 223 allows the tip of the mouldable material dispenser 500 to be fitted securely into the channel 220 but prevents the material dispenser from being over-inserted. This provides an interference fit around the tip to prevent mouldable material from escaping out of the channel 220 as it is being urged into the mouldable material carrier 200. The abutment 223 also helps a user to position the mouldable material dispenser 500 correctly to ensure effective transfer of the mouldable material into the mouldable material carrier 200.

Figure 9:
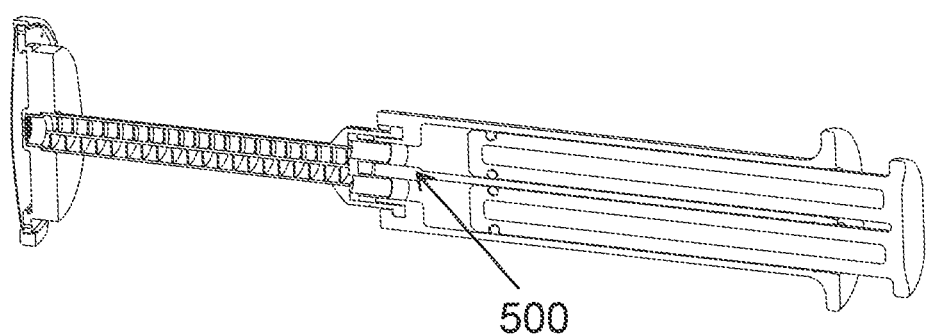
FIG. 9 shows a cross-sectional view of the mouldable material carrier in use with a syringe.

FIG. 9 shows a cross-sectional view of the mouldable material carrier 200 in use with a mouldable material dispenser 500. The mouldable material dispenser 500 fits into the channel 220 through the inlet 222. The abutment 223 prevents the tip of the mouldable material dispenser 500 from being over-inserted into the longitudinally running channel 220 that connects the inlet 222 to the outlet 224. The abutment 223 also provides a seal around the tip of the mouldable material dispenser 500 to prevent mouldable material from escaping out through the inlet as mouldable material is being injected into the mouldable material carrier 200.

When mouldable material is injected into the inlet 222 it passes through the channel 220 and is urged out of the outlet 224 to be distributed inside the cavity 242 of the mouldable material carrier 200.

The mouldable material carrier 200 described with reference to FIGS. 2-8 is only one embodiment. There are many different arrangements that can allow the mouldable material to be distributed evenly across the cavity 242 of the mouldable material holder 200. For instance, the channel 220 may be substantially frusto conical, having tapered walls such that its diameter reduces along its length. This arrangement would also prevent over-insertion of the mouldable material dispenser 500.

Figure 10:
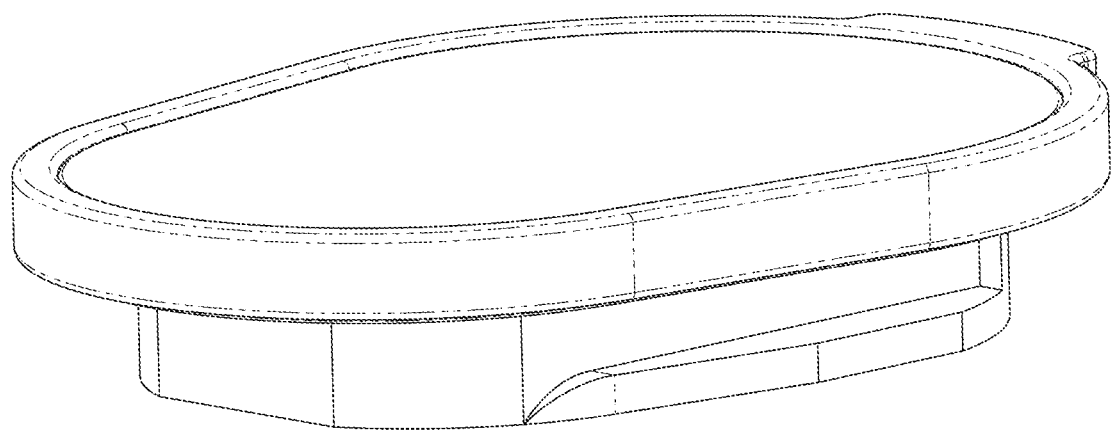
FIG. 10 shows a perspective view of the mouldable material carrier prior to the insertion of mouldable material.

FIG. 10 shows a perspective view of the mouldable material carrier 200 prior to the insertion of mouldable material. Prior to use, no mouldable material is present within the volume 240 and the flexible sheet 300 lies flat across the front of the mouldable material carrier.

Figure 11:
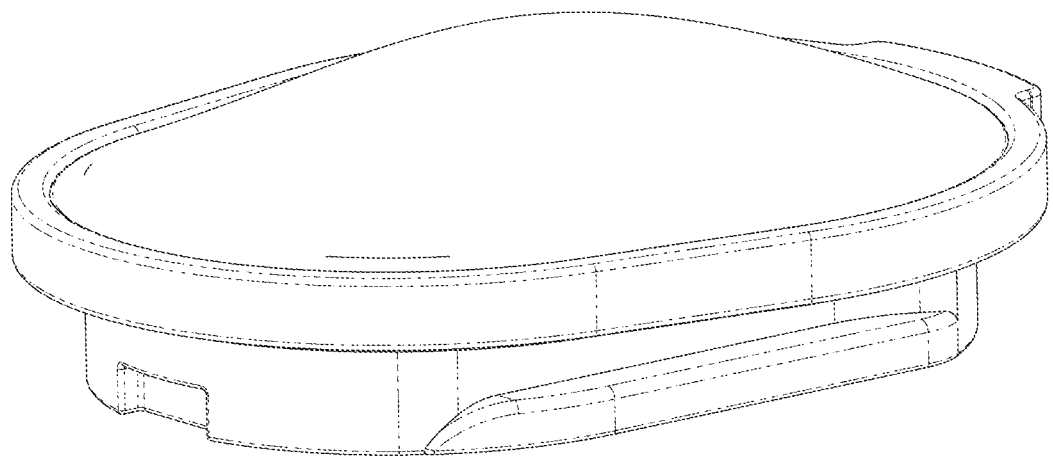
FIG. 11 shows a perspective view of the mouldable material carrier after the insertion of mouldable material.

FIG. 11 shows a perspective view of the mouldable material carrier after the insertion of mouldable material. The mouldable material carrier 200 has sufficient mouldable material inside the volume 240 to deform the flexible sheet 300. The mouldable material, contained within the flexible sheet 300, protrudes through the opening 111 in the retaining ring 400 so that an impression of the surgical site may be taken through the flexible sheet 300. The mouldable material forms a dome shape. Optionally, a user may add additional mouldable material to increase the surface area of the flexible sheet 300 to take an impression of a larger surgical site.

Whilst the above embodiments relate to securing a flexible sheet via a securing portion in the form of a retaining ring that secures over the lip of the base of the mouldable material carrier, in alternative embodiments, the flexible sheet is configured to be secured over the base through the elasticity of the flexible sheet itself. For instance, the flexible sheet may comprise an opening that is narrower than the cross-section of the base. As the flexible sheet in this embodiment is elastic, the flexible sheet may be stretched over the base and secured to the base via the elasticity of the flexible sheet. This provides a simpler arrangement for securing the flexible sheet to the base. In this case, the periphery of the base, over which the flexible sheet is secured, may be considered the securing portion. Alternatively, or in addition, the elasticated opening of the flexible sheet may be considered the securing portion.

Further Embodiments

The following description below relates to further embodiments of the invention. Whilst the above description includes embodiments in which the securing portion is separate to the base and flexible sheet (e.g. in the form of a ring that secures around the periphery of the base), the securing portion may instead form part of the flexible sheet and/or the base.

For instance, the securing portion may form part of the flexible sheet.

In an example, the contact between a surface of the base and the flexible sheet itself provides enough resistance to seal the mouldable material within the volume defined by the flexible sheet and the base.

For example, the flexible sheet can comprise of an opening that is smaller than a cross-section of the base and having an elasticity, such that the flexible sheet forms a seal around the base when stretched over the base. In this example, the cross-section of the flexible requires to be stretched to cover the cross-section of the base. The periphery of the opening will consequently be in contact with the base and held together by a reactionary force generated by the elasticity of the flexible sheet. The reactionary force on the base forms a seal between the surface of the base and the surface of the flexible sheet near the opening of the flexible sheet that prevents mouldable material from escaping the mouldable material carrier.

The elasticity of the flexible sheet and the friction present between the base and the surface of the flexible sheet may releasably secure the flexible sheet to the base. Accordingly, the removal of the flexible sheet may be achieved by simply pulling away the flexible sheet from the base. The removal of the flexible sheet may also be achieved by stretching the opening of the cross-section of the flexible and lifting the flexible sheet away from the base. The friction present between the base and the surface of the flexible sheet also provides a friction mechanism for preventing the flexible sheet from falling off the base, particularly when an impression of a surgical site is being taken, or has been taken.

Furthermore, the securing portion may form part of both the base and the flexible sheet.

In an example, the securing portion may form part of the base and the flexible sheet. In this case, the securing portion is formed of two sections, a first section that forms part of the flexible sheet and a second section that forms part of the base. The second section that forms part of the base may, for instance, form a groove and the first section that forms part of the flexible sheet may comprises a protruding portion, for instance, a lip or rim. The first section may fit within the second section, thereby forming an interference fit. In this case, the contact the protruding portion is secured within the groove and acts to seal the mouldable material in the volume defined by the flexible sheet and the base.

In one embodiment, the groove is formed along a periphery of the base. The groove may be along the whole perimeter of the base. For example, where the base has a circular, oval or elliptical cross-section, the groove may be along the whole perimeter of the cross-section (e.g. circumference). In some instances, the groove can be along a one or more portions of the perimeter of the base, with the flexible sheet having one or more corresponding protruding portions. Alternatively to the above, the base may have one or more protruding portions and the flexible sheet may form one or more corresponding holes or channels for receiving the one or more protruding portions.

The protruding portion can be present within, or attached to, the flexible sheet. The flexible sheet can comprise of an opening that is smaller than a cross-section of the base and smaller, or the same, than a cross-section of the groove. The protruding portion can be within, or attached to, the opening. The flexible sheet, in particular the opening, has an elasticity, such that the flexible sheet forms a seal by the contact between the protruding portion and the groove when the opening of the flexible is stretched over the base.

The seal is formed around the outlet and between the flexible sheet and the groove of the base; this ensures that mouldable material cannot escape from the volume formed by the flexible sheet and the base.

The protruding portion may be a rolled section of the flexible sheet. For example, the protruding portion can be a rolled section of the opening of the flexible sheet. The protruding portion may be an attachment to the flexible sheet. For example, the protruding portion can be an attached rim or frame around the opening of the flexible sheet.

The groove and protruding portion provides a lock mechanism for locking the flexible sheet to the base. The lock between the groove and the protruding portion provides a clutch for preventing the flexible sheet from falling off the base, particularly when an impression of a surgical site is being taken, or has been taken.

To provide a secure lock, the width of the groove must be sufficient to allow entry of the protruding portion, but narrow enough to provide a resilient abutment for the protruding portion thereby forming an interference fit. For example, the width of the groove may be at least half the thickness of the protruding portion. In some instances, the width of the groove may be larger than half the thickness of the protruding portion, but still narrower than the width of the protruding portion. The abutment provided by the sidewalls from the width of the groove creates a tighter confinement of the mouldable material inside the volume.

In another example, the securing portion may form part of the base and the flexible sheet, wherein the part of the base comprises a securing surface running around the periphery of the base and the part of the flexible sheet comprises a tightening portion. The tightening portion may be a spring, or band or clamp within or attached to the flexible sheet. The tightening portion holds the flexible sheet against the securing surface. The contact between the securing surface and the tightening portion seals the mouldable material in the volume defined by the flexible sheet and the base.

Forming a seal around the outlet, between the tightening portion and the securing surface ensures that mouldable material cannot escape from the volume formed by the tightening portion and the securing surface. The force exerted by the tightening portion on the securing surface results in a tighter confinement of the mouldable material inside the volume. Moreover, the tightening portion may be adjusted to any height of the securing surface along the base, which allows variability in the volume formed by the flexible sheet and the base.

The tightening portion is placed along a section of the securing surface. The tightening portion may be contact the whole perimeter of the securing surface. For example, where the base is of a cylindrical shape, the tightening portion may contact the whole perimeter of the cylindrical surface (circumference) of the cylindrical shape. In some instances, the tightening portion can be in contact with only a portion of the perimeter of the base, for example via a clamp.

The securing surface is the part of the base that that receives the force exerted by the tightening portion. The securing surface could be any surface of the base. The securing surface has sufficient mechanical hardness or resilience to provide resistance to the force exerted by the tightening portion such that the base does not result in permanent deformation by the force exerted by the tightening portion.

The seal is formed around the outlet and between the tightening portion and the securing surface; this ensures that mouldable material cannot escape from the volume formed by the flexible sheet and the base.

The tightening portion enables the flexible sheet to be releasably secured to the base. The tightening portion may be untightened to release the flexible sheet from base. The tightening portion may be sufficiently stretched such that the force exerted by the tightening portion is removed off the flexible sheet so that the flexible sheet may be detached from the base.

The tightening portion provides a fastening mechanism for holding the flexible sheet against the base. The grip between the tightening portion and the securing surface provides a hold for preventing the flexible sheet from falling off the base, particularly when an impression of a surgical site is being taken, or has been taken.

To provide a secure grip, the tightening portion must provide a large force without permanently distorting the securing surface. For example, where the tightening portion is a spring or band within or attached to the flexible sheet, a spring or band having high elasticity would provide a sufficient force to provide a seal and secure the flexible sheet to the base.

In another example, the securing portion may form part of the base and the flexible sheet, wherein the part of the base comprises a groove and a securing surface and the part of the flexible sheet comprises a tightening portion, in accordance with the examples as described above.

In another example, the securing portion may form part of the base and the flexible sheet, wherein the part of the base comprises a groove and a securing surface and the part of the flexible sheet comprises a protruding portion and a tightening portion, in accordance with the examples as described above.

In another example, the securing portion may form part of the base and the flexible sheet, wherein the part of the base is a securing surface and the part of the flexible sheet is an expanding portion. In an example, the expanding portion may be a coil. In an example, the coil may be within or attached to the flexible sheet. In an example, the expanding portion may be a portion of the flexible sheet itself having sufficient resilience to contain the mouldable material within the volume defined by the flexible sheet and the base.

The mouldable material is sealed by the contact between securing surface and the expanding portion. The securing surface can be the sidewalls of the cavity of the mouldable material carrier having sufficient resilience to withstand the expanding force of the expanding portion.

For example, in the example wherein the expanding portion is a coil, the coil may be placed inside the mouldable material carrier in a compressed state and the flexible sheet may be placed between the outer surface of the coil and the sidewalls of the cavity. After placement of the flexible sheet between the outer surface of the coil and cavity, the coil will naturally expand and generate a lateral force on the flexible sheet on the cavity of the base.

Where the expanding portion is the flexible sheet itself, or where the coil resides inside the flexible sheet, the flexible sheet may be placed inside the cavity of the base in a compressed state and the expanding force of the flexible sheet will define the volume for the mouldable material to be situated, which is sealed by the outer surface of the flexible sheet and the cavity of the base.

The expanding portion may be of reduced dimensions such that it will be situated underneath the at least one protrusion which protrudes laterally into the cavity from the wall surrounding the cavity. In this way, the sides of the cavity may be configured to resist transverse movements of the expanding member and the at least one protrusion protruding laterally into the cavity may be configured to resist longitudinal movements of the expanding movement.

The elasticity of the flexible sheet may vary across the area of the flexible sheet, depending on the securing portion.

For example, in the example wherein the securing portion is the contact between the base and the flexible sheet itself, it may be advantageous to have higher elasticity towards the edges of the flexible sheet and lower elasticity towards the centre of the flexible sheet. The higher elasticity towards the edges may provide a tighter confinement for the mouldable material inside the volume formed by the flexible sheet and the base due to the increased force on the base by the flexible sheet provided by the higher elasticity around its edges, as the edges of the flexible sheet will be the contact points between the flexible sheet and the base. The lower elasticity towards the centre of the flexible sheet may allow a larger amount of mouldable material to be inserted to mouldable material carrier due to a lowered force requirement for the mouldable material to expand the volume formed by the flexible sheet and the base provided by the lower elasticity toward its centre. A greater amount of mouldable material may, in some instances, enable a better impression of the surgical site to be taken.

In addition, whilst the above embodiments include a channel formed within the base for providing an inlet for providing mouldable material into the volume, in alternative embodiments, this channel may not be present. Instead, the channel may be formed within the flexible sheet. Alternatively, no channel may be provided, and the mouldable material may instead be placed on the base before the flexible sheet is secured over the mouldable material.

While certain arrangements have been described, the arrangements have been presented by way of example only, and are not intended to limit the scope of protection. The inventive concepts described herein may be implemented in a variety of other forms. In addition, various omissions, substitutions and changes to the specific implementations described herein may be made without departing from the scope of protection defined in the following claims.

The invention claimed is:
1. A mouldable material carrier for use in producing an impression of a surgical site comprising:
   a base having a channel passing through the base between an inlet and an outlet; and a securing portion configured to secure a flexible sheet to the base around the outlet to cover the outlet such that, when mouldable material is urged through the inlet, the mouldable material is extruded out of the outlet and contained within a volume defined by the flexible sheet and the base, such that when the mouldable material carrier is urged against the surgical site, the mouldable material within the volume forms an impression of the surgical site without making contact with the surgical site.

2. The mouldable material carrier according to claim 1, wherein the securing portion is configured to form a seal around the outlet between the flexible sheet and the base.

3. The mouldable material carrier according to claim 1, wherein the flexible sheet is secured to the base to cover the outlet.

4. The mouldable material carrier according to claim 1, wherein the flexible sheet is elastic.

5. The mouldable material carrier according to claim 1, wherein the outlet comprises at least one hole of reduced dimensions relative to the channel to resist the mouldable material from escaping the volume through the channel after the mouldable material has been urged into the volume.

6. The mouldable material carrier according to claim 5, wherein at the at least one hole is a plurality of holes formed via a grating provided at the outlet.

7. The mouldable material carrier according to claim 6, wherein the plurality of holes are evenly distributed across the outlet.

8. The mouldable material carrier according to claim 1, wherein the volume is at least partly defined by the flexible sheet and a cavity formed within the base and around the outlet.

9. The mouldable material carrier according to claim 8, wherein the base comprises at least one protrusion into the cavity to couple the mouldable material to the mouldable material carrier and resist removal of the mouldable material from the cavity after the mouldable material has been urged into the cavity.

10. The mouldable material carrier according to claim 1, wherein the channel is narrower at the outlet as compared to the inlet.

11. The mouldable material carrier according to claim 1, wherein at least one air hole is formed through the base such that air within the volume can escape the volume through the at least one air hole as the mouldable material is urged into the volume.

12. The mouldable material carrier according to claim 1, wherein the securing portion comprises an opening through which the flexible sheet is exposed when the flexible sheet is secured to allow an impression to be taken through the flexible sheet.

13. The mouldable material carrier according to claim 1, wherein the securing portion forms part of one or both of the flexible sheet and the base.

14. The mouldable material carrier according to claim 1, wherein the securing portion is configured to releasably secure the flexible sheet to the base.

15. The mouldable material carrier according to claim 14, wherein the securing portion comprises a finger release tab for aiding a user to release the securing portion to separate the flexible sheet from the base.

16. The mouldable material carrier according to claim 14, wherein the securing portion is separable from the base and is configured to be secured over the base to releasably secure the flexible sheet to the base.

17. The mouldable material carrier according to claim 1, wherein the base further comprises a coupling portion configured to couple the base to a production apparatus in a predetermined position and orientation so that, after an impression of a surgical site has been taken, a configuration of surface of the mouldable material can be recorded with respect to a known point of reference.

18. A kit of parts for producing a mouldable material carrier for use in obtaining an impression of a surgical site, including:
   a flexible sheet;
   a base having a channel passing through the base between an inlet and an outlet; and
   a securing portion configured to secure the flexible sheet to the base around the outlet to cover the outlet such that, when mouldable material is urged through the inlet, the mouldable material is extruded out of the outlet and contained within a volume defined by the flexible sheet and the base, such that when the mouldable material carrier is urged against a surgical site, the mouldable material within the volume forms an impression of the surgical site without making contact with the surgical site.

19. A kit of parts according to claim 18, wherein one or both of:
   the kit of parts further comprises mouldable material for being placed against a surgical site to form an impression of that site, and the securing portion forms part of one or both of the flexible sheet and the base.

* * * * *